United States Patent
Zywiak et al.

(10) Patent No.: US 9,816,720 B2
(45) Date of Patent: Nov. 14, 2017

(54) HEAT EXCHANGER CONTAMINATION MONITORING

(71) Applicant: Hamilton Sundstrand Corporation, Windsor Locks, CT (US)

(72) Inventors: Thomas M. Zywiak, Suffield, CT (US); Jason S. Yim, South Windsor, CT (US)

(73) Assignee: HAMILTON SUNDSTRAND CORPORATION, Windsor Locks, CT (US)

( * ) Notice: Subject to any disclaimer, the term of this patent is extended or adjusted under 35 U.S.C. 154(b) by 534 days.

(21) Appl. No.: 14/554,333

(22) Filed: Nov. 26, 2014

(65) Prior Publication Data

US 2016/0146487 A1 May 26, 2016

(51) Int. Cl.
*G01N 25/00* (2006.01)
*G01K 13/00* (2006.01)
(Continued)

(52) U.S. Cl.
CPC ........ *F24F 11/001* (2013.01); *F24D 19/1084* (2013.01); *F24F 11/006* (2013.01);
(Continued)

(58) Field of Classification Search
USPC ............................ 374/110, 142, 45, 165, 166
See application file for complete search history.

(56) References Cited

U.S. PATENT DOCUMENTS 8,902,071 B2 * 12/2014 Barton .................. F24F 12/001
219/667
2005/0159846 A1 7/2005 Van Ostrand et al.
(Continued)

FOREIGN PATENT DOCUMENTS

GB 2257244 A 1/1993
WO 2013055080 A1 4/2013

OTHER PUBLICATIONS

Extended European Search Report of the European Patent Office for International Application No. EP15196567, May 2, 2016, 5 pages.

*Primary Examiner* — Mirellys Jagan
(74) *Attorney, Agent, or Firm* — Cantor Colburn LLP (57) ABSTRACT

Embodiments relate to heat exchanger contamination monitoring in an air conditioning system. An aspect includes receiving, by a contamination monitoring logic from a primary heat exchanger outlet temperature sensor, a first temperature comprising an air temperature at an outlet of a primary heat exchanger. Another aspect includes receiving, from a secondary heat exchanger outlet temperature sensor, a second temperature comprising an air temperature at an outlet of a secondary heat exchanger. Another aspect includes receiving, from a compressor outlet temperature sensor, a third temperature comprising an air temperature at an outlet of a compressor. Another aspect includes determining, based on the first, second, and third temperature, a heat exchanger contamination value. Another aspect includes comparing the heat exchanger contamination value to a predetermined contamination threshold. Another aspect includes based on the heat exchanger contamination value being greater than the predetermined contamination threshold, sending a maintenance warning.

20 Claims, 8 Drawing Sheets

(51) Int. Cl.
*G01K 3/00* (2006.01)
*G01K 7/00* (2006.01)
*F24F 11/00* (2006.01)
*F24D 19/10* (2006.01)

(52) U.S. Cl.
CPC .......... *F24F 11/0086* (2013.01); *G01N 25/00* (2013.01); *F24D 2220/04* (2013.01); *F24F 2011/0045* (2013.01); *F24F 2011/0052* (2013.01); *F24F 2011/0063* (2013.01); *F24F 2011/0068* (2013.01); *F24F 2011/0075* (2013.01); *F24F 2011/0091* (2013.01)

(56) References Cited

U.S. PATENT DOCUMENTS

2012/0221150 A1* 8/2012 Arensmeier ....... G05B 23/0224
700/276
2015/0345821 A1* 12/2015 Alsaleem ............... F24F 11/001
374/147
2016/0003509 A1* 1/2016 Pistone .................. G01K 13/00
29/890.031
2016/0334127 A1* 11/2016 Rupp ..................... G05B 15/02

* cited by examiner

HEAT EXCHANGER CONTAMINATION MONITORING

BACKGROUND

This disclosure relates generally to air conditioning systems, and more particularly to monitoring of a heat exchanger of an air conditioning system for contamination.

In an air conditioning system, ambient air, or ram air, is drawn through a ram air inlet duct into the heat exchanger by a ram air fan. The ambient air may contain contaminants, which may range from particulate such as tree pollen to larger contaminants such as raincoats or birds. Such contaminants may build up or be caught in or on the heat exchanger fins and block airflow through the heat exchanger, thereby increasing the pressure drop across the heat exchanger. Such conditions may cause the ram air fan to operate in an unstable operating mode which may cause excessive blade stress and result in ram fan failure. For an air conditioning system in an aircraft, in order to avoid such ram fan failures, the operator of the aircraft may reduce the time between cleaning intervals of the heat exchanger; however, the reduced cleaning intervals may increase operating costs for the aircraft.

SUMMARY

Embodiments relate to heat exchanger contamination monitoring in an air conditioning system. An aspect includes receiving, by a contamination monitoring logic from a primary heat exchanger outlet temperature sensor, a first temperature comprising an air temperature at an outlet of a primary heat exchanger of the air conditioning system. Another aspect includes receiving, by the contamination monitoring logic from a secondary heat exchanger outlet temperature sensor, a second temperature comprising an air temperature at an outlet of a secondary heat exchanger of the air conditioning system. Another aspect includes receiving, by the contamination monitoring logic from a compressor outlet temperature sensor, a third temperature comprising an air temperature at an outlet of a compressor of the air conditioning system, wherein the compressor receives airflow from the outlet of the primary heat exchanger, and wherein the secondary heat exchanger receives airflow from the outlet of the compressor. Another aspect includes determining, by the contamination monitoring logic, based on the first temperature, the second temperature, and the third temperature, a heat exchanger contamination value. Another aspect includes comparing the heat exchanger contamination value to a predetermined contamination threshold. Another aspect includes based on the heat exchanger contamination value being greater than the predetermined contamination threshold, sending a maintenance warning to an operator of the air conditioning system.

Additional features are realized through the techniques of the present exemplary embodiment. Other embodiments are described in detail herein and are considered a part of what is claimed. For a better understanding of the features of the exemplary embodiment, refer to the description and to the drawings.

BRIEF DESCRIPTION OF THE SEVERAL VIEWS OF THE DRAWINGS

Referring now to the drawings wherein like elements are numbered alike in the several FIGURES.

DETAILED DESCRIPTION

Embodiments of heat exchanger contamination monitoring are provided, with exemplary embodiments being discussed below in detail. In order to prevent damage to the ram fan, the amount of heat exchanger contamination is determined and monitored so that, when a contamination threshold is exceeded, the operator is notified of the pending problem so that maintenance of the heat exchanger may be scheduled. The notification may be issued in advance of when the need for maintenance becomes critical, allowing the operator of an aircraft that includes the air conditioning system to schedule the maintenance while reducing disruption to use of the aircraft.

As contamination levels in the heat exchangers increase, the heat transfer properties of the heat exchangers will degrade causing various system parameter values to change from expected typical performance levels. Ambient conditions will also have an influence on these parameter values. Performance criteria to monitor changes in airflow, valve position, compressor outlet temperature, condenser inlet temperature, and heat exchanger effectiveness as a function of ambient conditions are used to quantify contamination levels in a contamination monitoring logic. Once operating conditions have exceeded beyond a predetermined contamination threshold, a maintenance message can be sent to the maintenance personnel. Cleaning of the heat exchangers to remove the contamination can then be scheduled within a reasonable time period to avoid interruptions caused by hardware failures in the air conditioning system. Premature heat exchanger removal and cleaning may also be avoided, thereby increasing the time on-wing of the aircraft and reducing operating costs for the aircraft. In some embodiments, if the system is allowed to exceed a secondary threshold for contamination after the maintenance message has been sent, the air conditioning system may be controlled into a reduced operating mode in order to prevent hardware failure.

Figure 1:
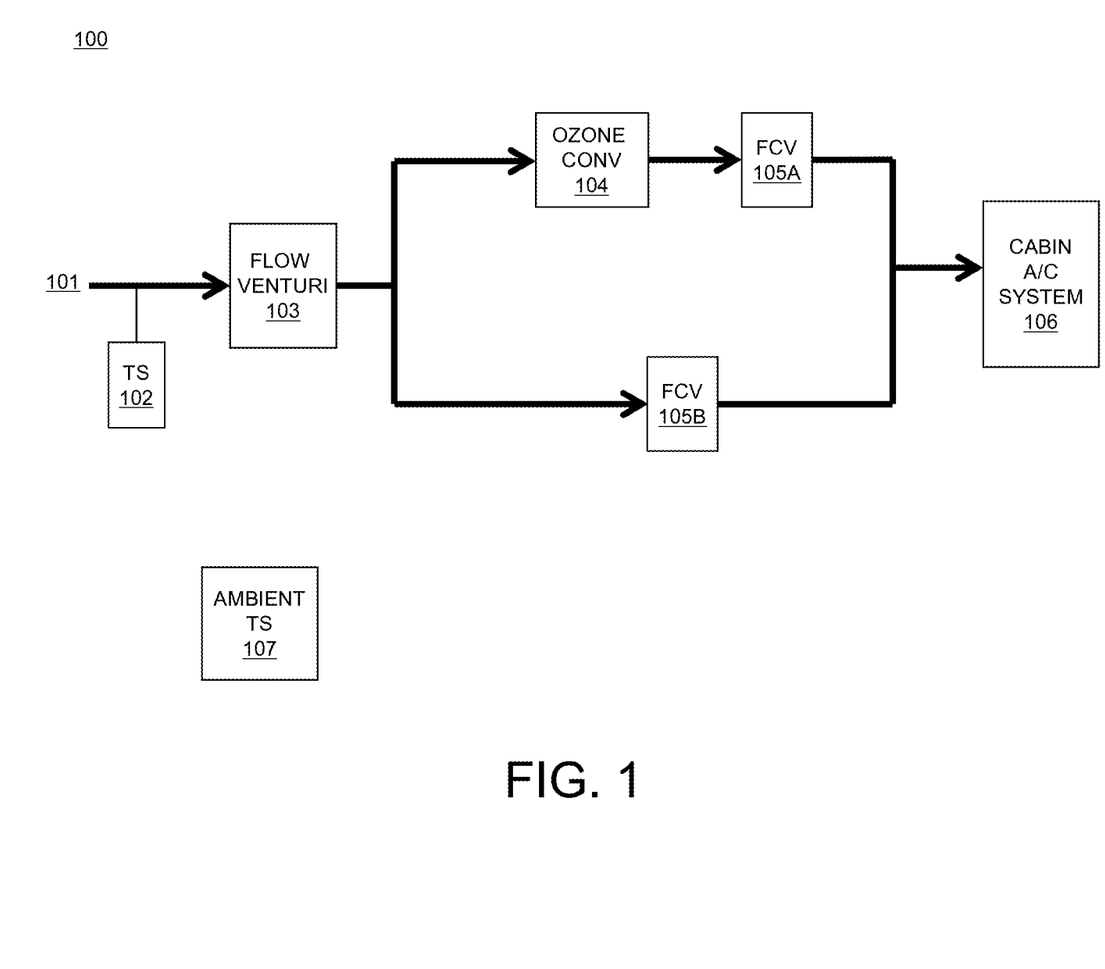
FIG. 1 illustrates an embodiment of an air inlet system for an air conditioning system for an aircraft in which heat exchanger contamination monitoring is implemented.

FIG. 1 illustrates an embodiment of an air inlet system 100 for an air conditioning system for an aircraft in which heat exchanger contamination monitoring is implemented. Air inlet system 100 includes air inlet 101, which receives inlet air from, in various embodiments, the engine, the auxiliary power unit, or a cabin air compressor of the aircraft that includes the air conditioning system. System inlet temperature sensor (TS) 102 determines a temperature of the air that is received at air inlet 101, and provides the temperature of the air that is received at air inlet 101 to a heat exchanger contamination monitoring logic, which is discussed in further detail below with respect to FIG. 3. The air that is received at air inlet 101 passes through flow venturi 103, which includes an inlet flow sensor, and then passes through ozone converter 104 and flow control valve (FCV) 105A-B into the cabin air conditioning system 106, which is shown in detail below with respect to FIG. 2. The position of the FCV 105A-B is adjusted to route airflow through or around the ozone converter 104 based on the inlet flow sensor in the flow venturi 103. The position of the FCV 105A-B may be provided to the heat exchanger contamination monitoring logic. An ambient temperature sensor 107 is also shown in FIG. 1; the ambient temperature sensor 107 may be in any appropriate location on the outside of an aircraft that includes the air conditioning system, and the temperature that is determined by the ambient temperature sensor 107 is also provided to the air contamination monitoring logic.

Figure 2:
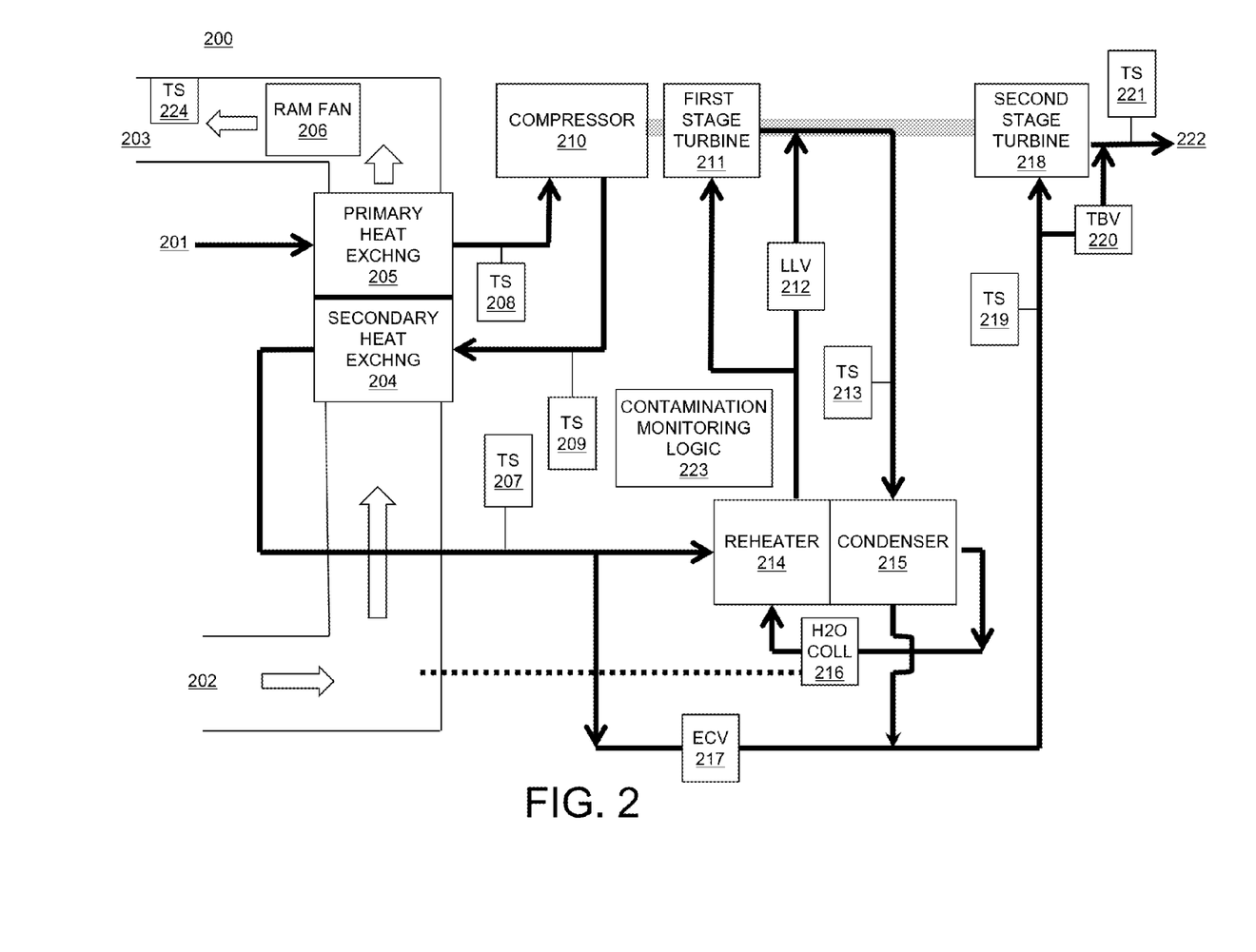
FIG. 2 illustrates an embodiment of an air conditioning system for an aircraft in which heat exchanger contamination monitoring is implemented.

FIG. 2 illustrates an embodiment of an air conditioning system 200 for an aircraft in which heat exchanger contamination monitoring is implemented. Air conditioning system 200 comprises air conditioning system 106 of FIG. 1. Air inlet 201 receives airflow from the FCV 105A-B that was shown in FIG. 1, and provides this airflow to the primary heat exchanger 205. The airflow is cooled in the primary heat exchanger 205, and proceeds out of the primary heat exchanger 205, past primary heat exchanger outlet temperature sensor 208, to the compressor 210. System airflow through primary heat exchanger 205 and secondary heat exchanger 204 are cooled by ambient airflow that is received on ambient airflow inlet 202, proceeds through both primary heat exchanger 205 and secondary heat exchanger 204, and exits the system 200 via ambient outlet 203. The ram fan 206 is located in the ambient airflow path after the primary heat exchanger 205. The ram fan may also include a flow sensor that provides a ram fan airflow value to the contamination monitoring logic 223.

Airflow exits the compressor 210 and proceeds past the compressor outlet temperature sensor 209 to the secondary heat exchanger 204. The airflow then exits the secondary heat exchanger 204, proceeds past the secondary heat exchanger outlet temperature sensor 207, and enters the reheater 214. Some airflow may bypass the reheater 214 via the economy cooling valve (ECV) 217 based on the position of the ECV 217, which may be adjusted based on operating conditions in the air conditioning system 200. The position of the ECV 217 may be provided to contamination monitoring logic 223. From the reheater 214, the airflow proceeds to the first stage turbine 211. Some airflow may bypass the first stage turbine 211 via the low limit valve (LLV) 212. The position of the LLV 212 may be adjusted based on operating conditions in the air conditioning system 200, and the position of the LLV 212 may be provided to contamination monitoring logic 223. From the outlet of the first stage turbine 211 and the LLV 212, the airflow then proceeds to the condenser 215, passing by the condenser inlet temperature sensor 213. Water that accumulates in the condenser 215 is sent to water collection 216, and sprayed into the ambient airflow inlet 202. Airflow exits the condenser 215 and proceeds to the second stage turbine 218, passing the second stage turbine inlet temperature sensor 219. Airflow from the ECV 217 also proceeds to the second stage turbine 218. The cooled airflow exits the second stage turbine at system outlet 222, passing the system outlet temperature sensor 221, and exiting the system 200 at system outlet 222. Some airflow may bypass the second stage turbine 218 and proceed directly to the system outlet temperature sensor 221 and system outlet 222 via the turbine bypass valve (TBV) 220. System outlet 222 may also include a flow sensor that provides a system outlet airflow value to the contamination monitoring logic 223. The position of the TBV 220 may be adjusted based on operating conditions in the air conditioning system 200, and the position of the TBV 220 may be provided to contamination monitoring logic 223.

Air conditioning system 200 includes a contamination monitoring logic 223, which receives inputs from the various temperature sensors and valves in air conditioning system 200, and in the air inlet system 100, in order to determine when to schedule maintenance to remove contamination from the primary heat exchanger 205 and secondary heat exchanger 204. Such maintenance may require an aircraft that includes the air conditioning system 200 to be out of service for, for example, a full day; therefore, a warning that maintenance needs to be scheduled may be issued well in advance of the maintenance being required. For example, a warning may be issued by contamination monitoring logic 223 that maintenance should be performed within the next month. Contamination monitoring logic 223 is discussed in further detail with respect to FIGS. 3 and 4.

In some embodiments, an additional temperature sensor comprising an ambient air outlet temperature sensor 224 is located at the ambient air outlet 203. The temperature information from the ambient air outlet temperature sensor 224 may be used to calculate the airflow rate in the ram fan 206. The heat rejection rate to the ram fan 206 may be determined based on data from the flow venturi 103 and the temperature sensors 102, 208, 209, and 207. The air flow rate at the ram fan 206 can then be calculated using the determined heat rejection rate, in conjunction with data from the ambient temperature sensor 107 and the ambient air outlet temperature sensor 224. In such an embodiment, the ambient air outlet temperature sensor 224 may replace the airflow sensor at the ram fan 206.

Figure 3:
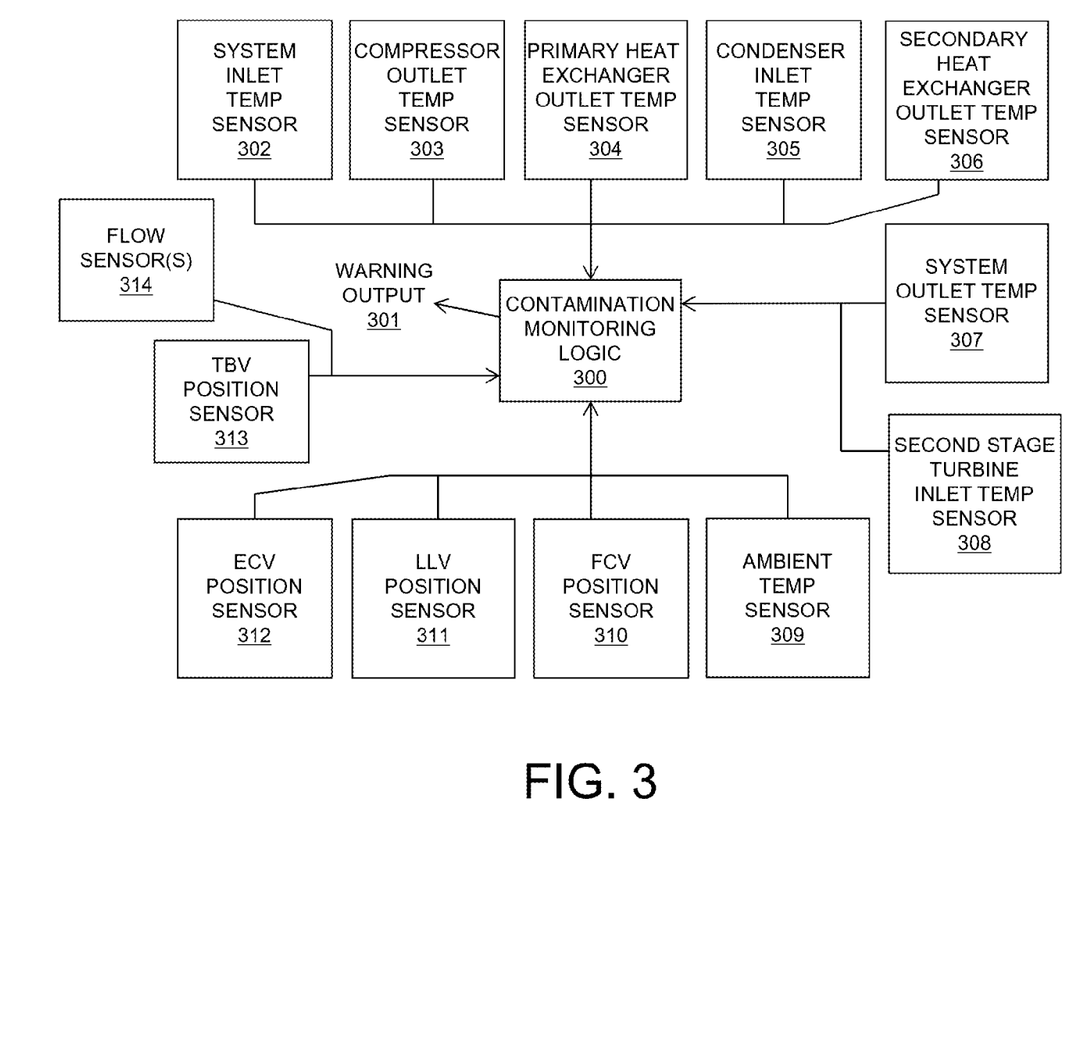
FIG. 3 illustrates an embodiment of a heat exchanger contamination monitoring logic.

FIG. 3 illustrates an embodiment of a heat exchanger contamination monitoring logic 300, which comprises contamination monitoring logic 223 of FIG. 2. The contamination monitoring logic 300 receives inputs comprising temperature data a plurality of temperature sensors, and position data from a plurality of valves, in the air conditioning system, in order to determine a degree of contamination of the primary and secondary heat exchangers 204 and 205. The system inlet temperature sensor 302 of FIG. 3 corresponds to TS 102 of FIG. 1. The compressor outlet temperature sensor 303 corresponds to TS 209 of FIG. 2. The primary heat exchanger outlet temperature sensor 304 corresponds to TS 208 of FIG. 2. The condenser inlet temperature sensor 305 corresponds to TS 213 of FIG. 2. The secondary heat exchanger outlet temperature sensor 306 corresponds to TS 207 of FIG. 2. The system outlet temperature sensor 307 corresponds to TS 221 of FIG. 2. The second stage turbine inlet temperature sensor 308 corresponds to TS 219 of FIG. 2. The ambient temperature sensor 309 corresponds to ambient TS 107 of FIG. 1. The FCV position sensor 310 corresponds to FCV 105A-B of FIG. 1. The LLV position sensor 311 corresponds to LLV 212 of FIG. 2. The ECV position sensor 312 corresponds to ECV 217 of FIG. 2. The TBV position sensor 313 corresponds to TBV 220 of FIG. 2. In further embodiments, the contamination monitoring logic 300 receives flow values from one or more flow sensors 314 in the air conditioning system; for example, flow sensors may be located in the ram fan 206 and at the system outlet 222. In some embodiments, an ambient air outlet temperature sensor 224 may replace the airflow senor at the ram fan 206. The contamination monitoring logic 300 may use any combination of these inputs to determine a degree of contamination of the primary and secondary heat exchangers 204 and 205, and may compare the degree of contamination to a predetermined contamination threshold in order to issue a maintenance scheduling warning on warning output 301. FIG. 3 is shown for illustrative purposes only; a contamination monitoring logic may receive any appropriate number of inputs from elements in an air conditioning system, and the inputs may be connected to the contamination monitoring logic in any appropriate manner.

Figure 4:
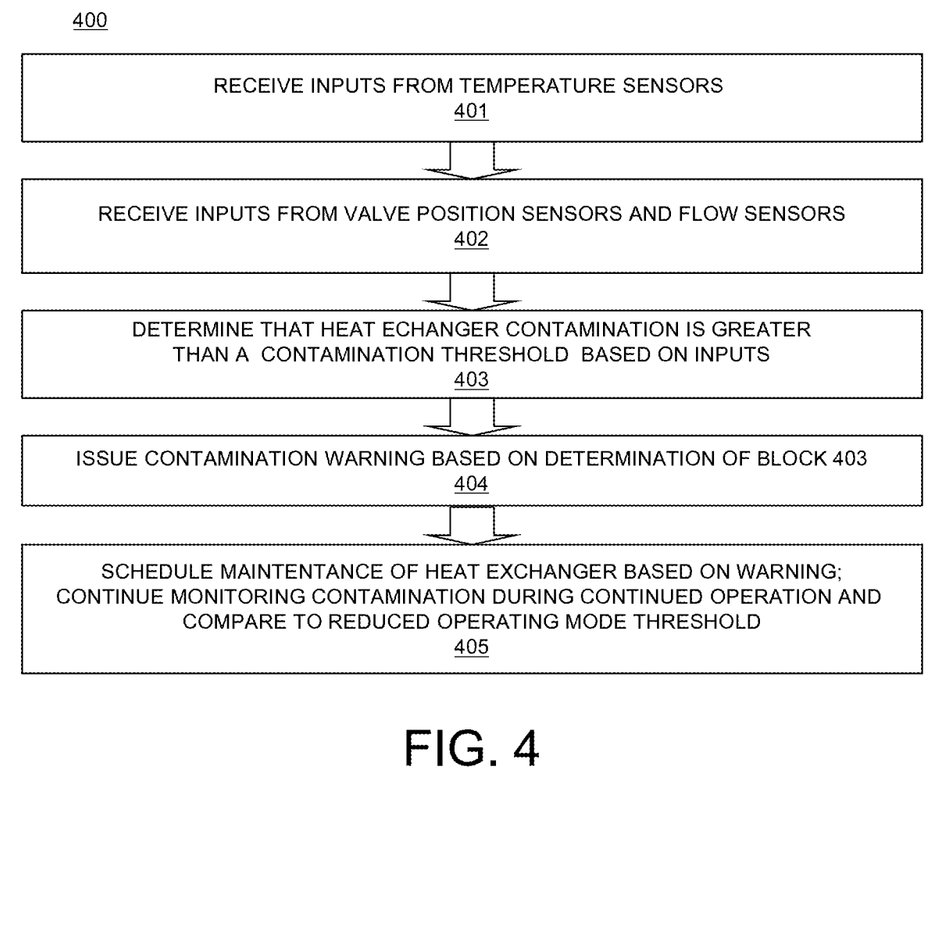
FIG. 4 illustrates an embodiment of a method for heat exchanger contamination monitoring in an air conditioning system.

FIG. 4 illustrates an embodiment of a method 400 for heat exchanger contamination monitoring in an air conditioning system. In block 401, the contamination monitoring logic 223/300 receives inputs from a plurality of temperature sensors in an air conditioning system 100/200 during operation of the air conditioning system. The temperature sensor inputs include a system inlet temperature, a compressor outlet temperature, a primary heat exchanger outlet temperature, a condenser inlet temperature, a secondary heat exchanger outlet temperature, a system outlet temperature, a second stage turbine inlet temperature, and an ambient temperature. In block 402, the contamination monitoring logic receives data from a plurality of valve position sensors. The valve position data may comprise fully open, fully closed, or any position between open and closed. The valves from which position data is received may include a FCV, a LLV, an ECV, and a TBV. In further embodiments, the contamination monitoring logic also receives flow data from one or more flow sensors in the air conditioning system, for example, flow sensors may be located at the ram fan and at the system outlet. In block 403, the contamination monitoring logic determines, based on the temperature and valve position data received in blocks 401 and 402, a degree of contamination of the primary and secondary heat exchangers 204 and 205. The degree of contamination indicates an amount of contaminants from the ambient airflow that have collected in and on the heat exchangers; these contaminants reduce the ambient airflow through the heat exchangers, increasing temperature levels and possibly causing unstable operation of the ram fan. The degree of contamination is monitored during operation of the air conditioning system and compared to a predetermined contamination threshold. In block 404, if the determined degree of contamination is greater than the predetermined contamination threshold, the contamination monitoring logic issues a maintenance needed warning. The warning allows an operator of an aircraft in which the air conditioning system is located to schedule maintenance of the heat exchangers. The warning may indicate an amount of time in which the maintenance should be scheduled. Lastly, in block 405, the operator schedules maintenance of the heat exchangers based on the warning. In some embodiments of block 405, as the air conditioning system continues to operate after exceeding the threshold of block 403 while waiting for maintenance, the contamination monitoring logic may continue to monitor and compare the contamination to another, higher threshold that comprises a reduced operating mode threshold. If, during the continued operation, the contamination surpasses the higher threshold, the air conditioning system may be controlled into the reduced operating mode in order to prevent hardware failure in the air conditioning system.

Figure 5:
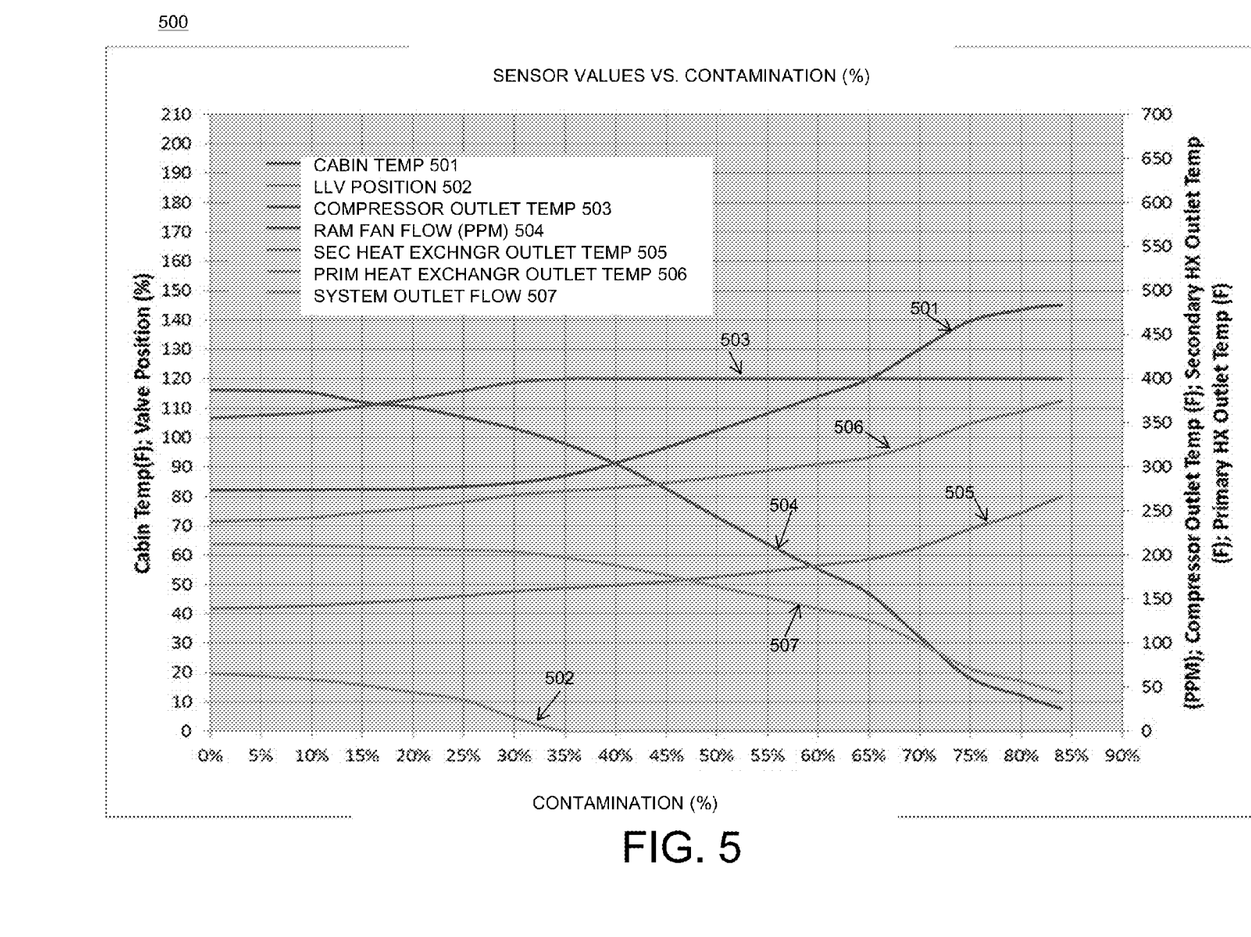
FIG. 5 illustrates a graph of example relationships between various sensor values and heat exchanger contamination.

FIG. 5 illustrates a graph 500 of example relationships between various sensor values, including temperature, valve position, and flow, and heat exchanger contamination. The heat exchanger contamination values range from 0% (clean) to 100% (cleaning recommended). As shown in FIG. 5, as heat exchanger contamination increases, secondary heat exchanger outlet temperature 505, cabin temperature (i.e., system outlet temperature) 501, primary heat exchanger outlet temperature 506, and compressor outlet temperature 503 also increase. Further, as heat exchanger contamination increases, the ram fan airflow 504 and the system outlet airflow 507 also decrease. LLV position 502, as shown in FIG. 5, is fully closed at about 35% contamination or higher. These relationships may be used to determine an amount of contamination of the heat exchangers by the contamination monitoring logic in block 403 of FIG. 4.

Figure 6:
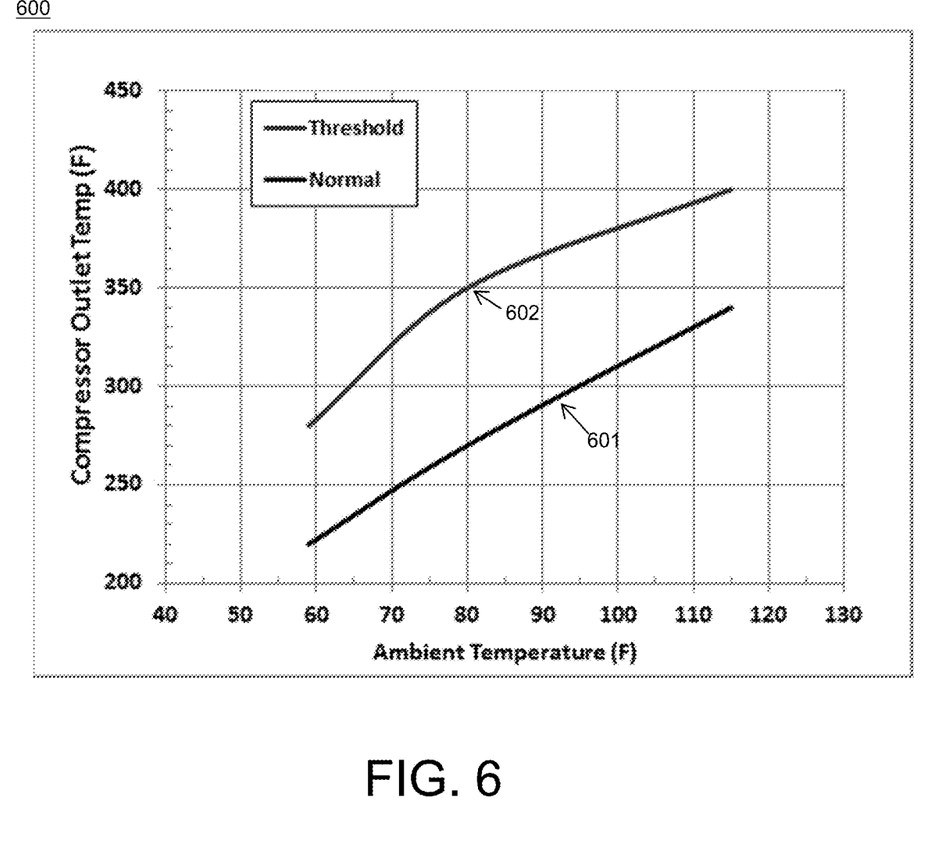
FIG. 6 illustrates a graph of an example relationship between compressor outlet temperature and ambient temperature under normal and contaminated conditions.

FIG. 6 illustrates a graph of an example relationship between compressor outlet temperature and ambient temperature for normal and threshold levels of heat exchanger contamination. The heat exchanger contamination values range from 0% (clean) to 100% (cleaning recommended). Line 601 indicates the relationship between compressor outlet temperature and ambient temperature under normal conditions, while line 602 shows the relationship between compressor outlet temperature and ambient temperature under threshold contamination conditions in the heat exchangers. These relationships may be used to determine whether the heat exchangers are at or near threshold conditions based on ambient and compressor outlet temperature in block 403 of FIG. 4.

Figure 7:
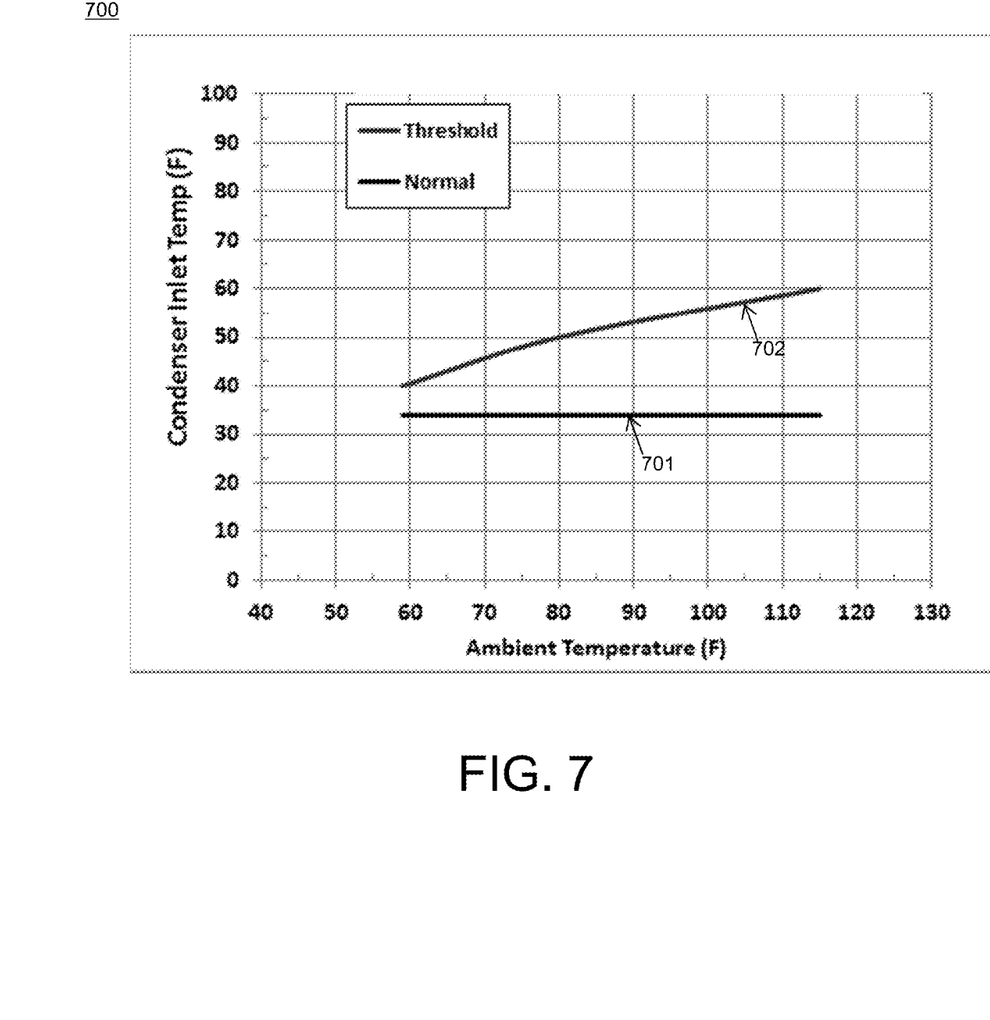
FIG. 7 illustrates a graph of an example relationship between condenser inlet temperature and ambient temperature under normal and contaminated conditions.

FIG. 7 illustrates a graph of an example relationship between condenser inlet temperature and ambient temperature for normal and threshold levels of heat exchanger contamination. The heat exchanger contamination values range from 0% (clean) to 100% (cleaning recommended). Line 701 indicates the relationship between condenser inlet temperature and ambient temperature under normal conditions, while line 702 shows the relationship between condenser inlet temperature and ambient temperature under threshold contamination conditions in the heat exchangers. These relationships may be used to determine whether the heat exchangers are at or near threshold conditions based on ambient and condenser inlet temperature in block 403 of FIG. 4.

Figure 8:
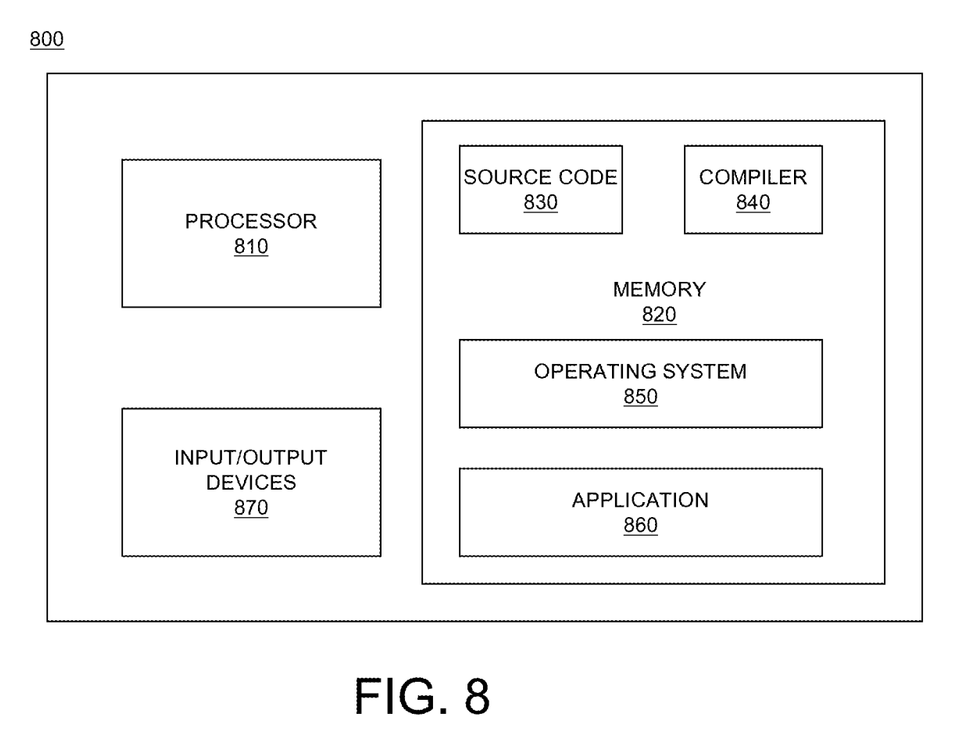
FIG. 8 illustrates an embodiment of a computer in which a heat exchanger contamination monitoring logic may be implemented.

FIG. 8 illustrates an embodiment of a computer 800 in which a heat exchanger contamination monitoring logic may be implemented. Various operations discussed above may utilize the capabilities of the computer 800. One or more of the capabilities of the computer 800 may be incorporated in any element, module, application, and/or component discussed herein. For example, embodiments of a receiver with a four-slice DFE may be incorporated into input/output (I/O) devices 870.

The computer 800 includes, but is not limited to, PCs, workstations, laptops, PDAs, palm devices, servers, storages, and the like. Generally, in terms of hardware architecture, the computer 800 may include one or more processors 810, memory 820, and one or more I/O devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a digital signal processor (DSP), or an auxiliary processor among several processors associated with the computer 800, and the processor 810 may be a semiconductor based microprocessor (in the form of a microchip) or a macroprocessor.

The memory 820 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the memory 820 may include one or more separate programs, each of which comprises an ordered listing of executable instructions for implementing logical functions. The software in the memory 820 includes a suitable operating system (O/S) 850, compiler 840, source code 830, and one or more applications 860 in accordance with exemplary embodiments. As illustrated, the application 860 comprises numerous functional components for implementing the features and operations of the exemplary embodiments. The application 860 of the computer 800 may represent various applications, computational units, logic, functional units, processes, operations, virtual entities, and/or modules in accordance with exemplary embodiments, but the application 860 is not meant to be a limitation.

The operating system 850 controls the execution of other computer programs, and provides scheduling, input-output control, file and data management, memory management, and communication control and related services. It is contemplated by the inventors that the application 860 for implementing exemplary embodiments may be applicable on all commercially available operating systems.

Application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, FORTRAN, COBOL, Perl, Java, ADA, .NET, and the like.

The I/O devices 870 may include input devices such as, for example but not limited to, a mouse, keyboard, scanner, microphone, camera, etc. Furthermore, the I/O devices 870 may also include output devices, for example but not limited to a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or intranet.

If the computer 800 is a PC, workstation, intelligent device or the like, the software in the memory 820 may further include a basic input output system (BIOS) (omitted for simplicity). The BIOS is a set of essential software routines that initialize and test hardware at startup, start the O/S 850, and support the transfer of data among the hardware devices. The BIOS is stored in some type of read-only-memory, such as ROM, PROM, EPROM, EEPROM or the like, so that the BIOS can be executed when the computer 800 is activated.

When the computer 800 is in operation, the processor 810 is configured to execute software stored within the memory 820, to communicate data to and from the memory 820, and to generally control operations of the computer 800 pursuant to the software. The application 860 and the O/S 850 are read, in whole or in part, by the processor 810, perhaps buffered within the processor 810, and then executed.

When the application 860 is implemented in software it should be noted that the application 860 can be stored on virtually any computer readable storage medium for use by or in connection with any computer related system or method. In the context of this document, a computer readable storage medium may be an electronic, magnetic, optical, or other physical device or means that can contain or store a computer program for use by or in connection with a computer related system or method.

The application 860 can be embodied in any computer-readable storage medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable storage medium" can be any means that can store the program for use by or in connection with the instruction execution system, apparatus, or device. The computer readable storage medium can be, for example but not limited to, an electronic, magnetic, optical, electromagnetic, or semiconductor system, apparatus, or a device.

More specific examples (a nonexhaustive list) of the computer-readable storage medium may include the following: an electrical connection (electronic) having one or more wires, a portable computer diskette (magnetic or optical), a random access memory (RAM) (electronic), a read-only memory (ROM) (electronic), an erasable programmable read-only memory (EPROM, EEPROM, or Flash memory) (electronic), an optical fiber (optical), and a portable compact disc memory (CDROM, CD R/W) (optical). Note that the computer-readable storage medium could even be paper or another suitable medium, upon which the program is printed or punched, as the program can be electronically captured, via for instance optical scanning of the paper or other medium, then compiled, interpreted or otherwise processed in a suitable manner if necessary, and then stored in a computer memory.

In exemplary embodiments, where the application 860 is implemented in hardware, the application 860 can be implemented with any one or a combination of the following technologies, which are well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The technical effects and benefits of exemplary embodiments include determination of an appropriate maintenance interval for a heat exchanger in an air conditioning system of an aircraft.

The terminology used herein is for the purpose of describing particular embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention claimed is:

1. A method for heat exchanger contamination monitoring in an air conditioning system, the method comprising:
   receiving, by a contamination monitoring logic from a primary heat exchanger outlet temperature sensor, a first temperature comprising an air temperature at an outlet of a primary heat exchanger of the air conditioning system;
   receiving, by the contamination monitoring logic from a secondary heat exchanger outlet temperature sensor, a second temperature comprising an air temperature at an outlet of a secondary heat exchanger of the air conditioning system;
   receiving, by the contamination monitoring logic from a compressor outlet temperature sensor, a third temperature comprising an air temperature at an outlet of a compressor of the air conditioning system, wherein the compressor receives airflow from the outlet of the primary heat exchanger, and wherein the secondary heat exchanger receives airflow from the outlet of the compressor;
   determining, by the contamination monitoring logic, based on the first temperature, the second temperature, and the third temperature, a heat exchanger contamination value;
   comparing the heat exchanger contamination value to a predetermined contamination threshold;
   based on the heat exchanger contamination value being greater than the predetermined contamination threshold, sending a maintenance warning to an operator of the air conditioning system.

2. The method of claim 1, further comprising:
   receiving, by the contamination monitoring logic from a ram fan flow sensor, a first flow value comprising an amount of airflow at a ram fan of the air conditioning system; and
   receiving, by the contamination monitoring logic from a system inlet or outlet flow sensor, a second flow value comprising an amount of airflow at the outlet of the air conditioning system;
   wherein the heat exchanger contamination value is further determined based on the first flow value and the second flow value.

3. The method of claim 1, further comprising, after sending the maintenance warning to an operator of the air conditioning system:
   comparing the heat exchanger contamination value to a reduced operating mode threshold, wherein the reduced operating mode threshold is higher than the predetermined contamination threshold; and
   based on the heat exchanger contamination value being greater than the reduced operating mode threshold, controlling the air conditioning system to a reduced operating mode.

4. The method of claim 1, further comprising:
   receiving, by the contamination monitoring logic from an ambient air outlet temperature sensor, an eighth temperature value comprising a temperature at an ambient air outlet of the air conditioning system; and
   determining an amount of airflow at a ram fan of the air conditioning system based on the eighth temperature value.

5. The method of claim 1, further comprising:
   receiving, by the contamination monitoring logic from a system inlet temperature sensor, a fourth temperature comprising an air temperature at an inlet of the air conditioning system;
   receiving, by the contamination monitoring logic from a condenser inlet temperature sensor, a fifth temperature comprising an air temperature at an inlet of a condenser of the air conditioning system; and
   receiving, by the contamination monitoring logic from a system outlet temperature sensor, a sixth temperature comprising an air temperature at an outlet of the air conditioning system;
   wherein the heat exchanger contamination value is further determined based on the fourth temperature, the fifth temperature, and the sixth temperature.

6. The method of claim 5, further comprising:
   receiving, by the contamination monitoring logic from a second stage turbine inlet temperature sensor, a seventh temperature comprising an air temperature at an inlet of a second stage turbine of the air conditioning system;
   wherein the heat exchanger contamination value is further determined based on the seventh temperature.

7. The method of claim 1, further comprising:
   receiving, by the contamination monitoring logic from a low limit valve (LLV) position sensor, a first valve position comprising a position of a LLV of the air conditioning system;
   wherein the heat exchanger contamination value is further determined based on the first valve position.

8. The method of claim 7, further comprising:
   receiving, by the contamination monitoring logic from a flow control valve (FCV) position sensor, a second valve position comprising a position of a FCV of the air conditioning system;

receiving, by the contamination monitoring logic from an economy cooling valve (ECV) position sensor, a third valve position comprising a position of a ECV of the air conditioning system; and receiving, by the contamination monitoring logic from a turbine bypass valve (TBV) position sensor, a fourth valve position comprising a position of a TBV of the air conditioning system;

wherein the heat exchanger contamination value is further determined based on the second valve position, the third valve position, and the fourth valve position.

9. A system for heat exchanger contamination monitoring in an air conditioning system, comprising:

a heat exchanger contamination monitoring logic configured to:

receive, from a primary heat exchanger outlet temperature sensor, a first temperature comprising an air temperature at an outlet of a primary heat exchanger of the air conditioning system;

receive, from a secondary heat exchanger outlet temperature sensor, a second temperature comprising an air temperature at an outlet of a secondary heat exchanger of the air conditioning system;

receive, from a compressor outlet temperature sensor, a third temperature comprising an air temperature at an outlet of a compressor of the air conditioning system, wherein the compressor receives airflow from the outlet of the primary heat exchanger, and wherein the secondary heat exchanger receives airflow from the outlet of the compressor;

determine, based on the first temperature, the second temperature, and the third temperature, a heat exchanger contamination value;

compare the heat exchanger contamination value to a predetermined contamination threshold;

based on the heat exchanger contamination value being greater than the predetermined contamination threshold, send a maintenance warning to an operator of the air conditioning system.

10. The system of claim 9, further comprising:

receiving, by the contamination monitoring logic from a ram fan flow sensor, a first flow value comprising an amount of airflow at a ram fan of the air conditioning system; and receiving, by the contamination monitoring logic from a system inlet or outlet flow sensor, a second flow value comprising an amount of airflow at the outlet of the air conditioning system;

wherein the heat exchanger contamination value is further determined based on the first flow value and the second flow value.

11. The system of claim 9, further comprising:

receiving, by the contamination monitoring logic from a system inlet temperature sensor, a fourth temperature comprising an air temperature at an inlet of the air conditioning system;

receiving, by the contamination monitoring logic from a condenser inlet temperature sensor, a fifth temperature comprising an air temperature at an inlet of a condenser of the air conditioning system; and receiving, by the contamination monitoring logic from a system outlet temperature sensor, a sixth temperature comprising an air temperature at an outlet of the air conditioning system;

wherein the heat exchanger contamination value is further determined based on the fourth temperature, the fifth temperature, and the sixth temperature.

12. The system of claim 11, further comprising:

receiving, by the contamination monitoring logic from a second stage turbine inlet temperature sensor, a seventh temperature comprising an air temperature at an inlet of a second stage turbine of the air conditioning system;

wherein the heat exchanger contamination value is further determined based on the seventh temperature.

13. The system of claim 9, further comprising:

receiving, by the contamination monitoring logic from a low limit valve (LLV) position sensor, a first valve position comprising a position of a LLV of the air conditioning system;

wherein the heat exchanger contamination value is further determined based on the first valve position.

14. The system of claim 13, further comprising:

receiving, by the contamination monitoring logic from a flow control valve (FCV) position sensor, a second valve position comprising a position of a FCV of the air conditioning system;

receiving, by the contamination monitoring logic from an economy cooling valve (ECV) position sensor, a third valve position comprising a position of a ECV of the air conditioning system; and receiving, by the contamination monitoring logic from a turbine bypass valve (TBV) position sensor, a fourth valve position comprising a position of a TBV of the air conditioning system;

wherein the heat exchanger contamination value is further determined based on the second valve position, the third valve position, and the fourth valve position.

15. A computer program product for implementing a contamination monitoring logic for a heat exchanger in an air conditioning system, the computer program product comprising:

a computer readable storage medium having program instructions embodied therewith, the program instructions readable by a processing circuit to cause the processing circuit to perform a method comprising:

receiving, by the contamination monitoring logic from a primary heat exchanger outlet temperature sensor, a first temperature comprising an air temperature at an outlet of a primary heat exchanger of the air conditioning system;

receiving, by the contamination monitoring logic from a secondary heat exchanger outlet temperature sensor, a second temperature comprising an air temperature at an outlet of a secondary heat exchanger of the air conditioning system;

receiving, by the contamination monitoring logic from a compressor outlet temperature sensor, a third temperature comprising an air temperature at an outlet of a compressor of the air conditioning system, wherein the compressor receives airflow from the outlet of the primary heat exchanger, and wherein the secondary heat exchanger receives airflow from the outlet of the compressor;

determining, by the contamination monitoring logic, based on the first temperature, the second temperature, and the third temperature, a heat exchanger contamination value;

comparing the heat exchanger contamination value to a predetermined contamination threshold;

based on the heat exchanger contamination value being greater than the predetermined contamination threshold, sending a maintenance warning to an operator of the air conditioning system.

16. The computer program product of claim 15, further comprising:
  receiving, by the contamination monitoring logic from a ram fan flow sensor, a first flow value comprising an amount of airflow at a ram fan of the air conditioning system; and
  receiving, by the contamination monitoring logic from a system inlet or outlet flow sensor, a second flow value comprising an amount of airflow at the outlet of the air conditioning system;
  wherein the heat exchanger contamination value is further determined based on the first flow value and the second flow value.

17. The computer program product of claim 15, further comprising:
  receiving, by the contamination monitoring logic from a system inlet temperature sensor, a fourth temperature comprising an air temperature at an inlet of the air conditioning system;
  receiving, by the contamination monitoring logic from a condenser inlet temperature sensor, a fifth temperature comprising an air temperature at an inlet of a condenser of the air conditioning system; and
  receiving, by the contamination monitoring logic from a system outlet temperature sensor, a sixth temperature comprising an air temperature at an outlet of the air conditioning system;
  wherein the heat exchanger contamination value is further determined based on the fourth temperature, the fifth temperature, and the sixth temperature.

18. The computer program product of claim 17, further comprising:
  receiving, by the contamination monitoring logic from a second stage turbine inlet temperature sensor, a seventh temperature comprising an air temperature at an inlet of a second stage turbine of the air conditioning system;
  wherein the heat exchanger contamination value is further determined based on the seventh temperature.

19. The computer program product of claim 15, further comprising:
  receiving, by the contamination monitoring logic from a low limit valve (LLV) position sensor, a first valve position comprising a position of a LLV of the air conditioning system;
  wherein the heat exchanger contamination value is further determined based on the first valve position.

20. The computer program product of claim 19, further comprising:
  receiving, by the contamination monitoring logic from a flow control valve (FCV) position sensor, a second valve position comprising a position of a FCV of the air conditioning system;
  receiving, by the contamination monitoring logic from an economy cooling valve (ECV) position sensor, a third valve position comprising a position of a ECV of the air conditioning system; and
  receiving, by the contamination monitoring logic from a turbine bypass valve (TBV) position sensor, a fourth valve position comprising a position of a TBV of the air conditioning system;
  wherein the heat exchanger contamination value is further determined based on the second valve position, the third valve position, and the fourth valve position.

\* \* \* \* \*